(12) United States Patent
Li et al.

(10) Patent No.: US 11,752,120 B2
(45) Date of Patent: Sep. 12, 2023

(54) USE OF SUCCINIC ACID IN INCREASING SENSITIVITY OF BACTERIA TO ANTIBIOTICS

(71) Applicant: SUN YAT-SEN UNIVERSITY, Guangdong (CN)

(72) Inventors: Hui Li, Guangdong (CN); Bo Peng, Guangdong (CN); Xuanxian Peng, Guangdong (CN)

(73) Assignee: SUN YAT-SEN UNIVERSITY, Guangdong (CN)

( * ) Notice: Subject to any disclaimer, the term of this patent is extended or adjusted under 35 U.S.C. 154(b) by 13 days.

(21) Appl. No.: 16/640,060

(22) PCT Filed: Jun. 12, 2018

(86) PCT No.: PCT/CN2018/090752
§ 371 (c)(1),
(2) Date: Feb. 19, 2020

(87) PCT Pub. No.: WO2019/178954
PCT Pub. Date: Sep. 26, 2019

(65) Prior Publication Data
US 2021/0128506 A1 May 6, 2021

(30) Foreign Application Priority Data
Mar. 20, 2018 (CN) .......................... 201810231615.3

(51) Int. Cl.
*A61K 31/194* (2006.01)
*A61K 45/06* (2006.01)
*A61P 31/04* (2006.01)
*A61K 31/43* (2006.01)

(52) U.S. Cl.
CPC ............ *A61K 31/194* (2013.01); *A61K 31/43* (2013.01); *A61P 31/04* (2018.01); *A61K 45/06* (2013.01)

(58) Field of Classification Search
CPC ........ A61K 31/194; A61K 45/06; A61P 31/04
See application file for complete search history.

(56) References Cited

FOREIGN PATENT DOCUMENTS

CN 105492004 4/2016

OTHER PUBLICATIONS

Kumar et al, Nano Biomed Eng 2015, vol. 7, Issue 2, pp. 62-74. (Year: 2015).*

(Continued)

*Primary Examiner* — Craig D Ricci
*Assistant Examiner* — Janet L Coppins
(74) *Attorney, Agent, or Firm* — JCIPRNET

(57) ABSTRACT

The present invention belongs to the technical field of medicine, and specifically relates to use of succinic acid in increasing sensitivity of bacteria to antibiotics. The present invention found that the succinic acid can increase proton motive force of bacteria, thereby increasing the number of antibiotics entering the bacteria, and eventually killing the bacteria. Therefore, the succinic acid can increase the sensitivity of bacteria to antibiotics, thereby overcoming the problem of bacterial drug resistance. Combining succinic acid with antibiotics can significantly improve the bactericidal effect of the antibiotics, which has better effects and higher safety and operability compared with only using antibiotics as antibacterial drugs at present.

8 Claims, 5 Drawing Sheets

A

B

C

(56) References Cited

OTHER PUBLICATIONS

Feng et al, Food Sci Biotechnol 2010, vol. 19(1), pp. 35-41. (Year: 2010).*
Web printout of Zelman, Robin thesis: https://www.brown.edu/research/labs/weinreich/sites/brown.edu.research.labs.weinreich/files/uploads/Effects%20of%20Drug%20Concentration%20on%20Persistance%20in%20Escherichia%20coli.pdf, pp. 1-26, published 2009. (Year: 2009).*
Zuroff et al, BMC Microbiology 2010, 10:185, pp. 1-10. (Year: 2010).*
"International Search Report (Form PCT/ISA/210) of PCT/CN2018/090752", dated Dec. 24, 2018, with English translation thereof, pp. 1-6.
Song, Zhijun, et al., "Bacterial Biofilm and Antibiotic Resistance," Progress in Natural Sciences, vol. 13, Oct. 2003, pp. 1015-1021.
Yin, Lin, "Research progress of carbapenem resistance mechanisms in *Escherichia coli*," Journal of Tropical Medicine, vol. 17, Sep. 2017, pp. 1263-1267.

\* cited by examiner

USE OF SUCCINIC ACID IN INCREASING SENSITIVITY OF BACTERIA TO ANTIBIOTICS

CROSS-REFERENCE TO RELATED APPLICATION

This application is a 371 of international application of PCT application serial no. PCT/CN2018/090752, filed on Jun. 12, 2018, which claims the priority benefit of China application no. 201810231615.3, filed on Mar. 20, 2018. The entirety of each of the above mentioned patent applications is hereby incorporated by reference herein and made a part of this specification.

BACKGROUND

Technical Field

The present invention belongs to the technical field of medicine, and in particular, to use of succinic acid in increasing sensitivity of bacteria to antibiotics.

Description of Related Art

Pathogenic bacteria seriously endanger human health and sustainable development of the breeding industry, and are needed to be prevented and controlled by adopting effective measures. Since Fleming discovered penicillin in 1929, a large number of studies on various antibiotics have opened the era of antibiotics in humans, and various antibiotics have played a significant role in the treatment of infectious diseases, making the use of antibiotics increasingly widespread. Although the use of antibiotics can effectively prevent and treat diseases, the abuse and misuse of antibiotics can cause bacteria to develop drug resistance. Drug-resistant strains develop resistance to antibiotics that are originally effective, making infection difficult to control. Therefore, it is of great importance to adopt new methods to control infection of bacteria, especially drug-resistant bacteria.

The current research hotspot is to increase the sensitivity of drug-resistant bacteria to antibiotics, so that antibiotics which are originally ineffective or in low efficiency become effective and kill the drug-resistant bacteria. In recent years, it has been found that some small molecules can act in synergy with antibiotics to promote bactericidal effects, and preparing them with antibiotics into compound preparation is of great significance for controlling infection of bacteria, especially drug-resistant bacteria.

Succinic acid is an important four-carbon dicarboxylic acid intermediate in the tricarboxylic acid cycle, and it is also a degradation product of certain amino acids. A natural source of succinic acid is amber, etc., which is formed by the resin of *Pinus* plants buried in the ground for a long time, and it is also widely present in many plants and tissues of animals. In the medicine industry, succinic acid can be used to synthesize antidotes, diuretics, sedatives, hemostatics, antispasmodics, expectorants, sulfonamides, antibiotics, and vitamins A and B, etc. Succinic acid can also be used as a chemical reagent, as a standard reagent for alkalimetry, a buffer, and a comparison sample for gas chromatography. In the food industry, succinic acid can be used as flavoring agents, sour agents, buffering agents, for ham, sausages, aquatic products, flavoring liquids, etc. It can also be used as preservatives, pH value regulators and co-solvents. However, it has not been reported whether succinic acid can increase sensitivity of bacteria to antibiotics.

SUMMARY

In order to overcome the above-mentioned shortcomings of the prior art, the present invention provides use of succinic acid in increasing sensitivity of bacteria to antibiotics. The present invention found that succinic acid can increase the sensitivity of bacteria to antibiotics, thereby overcoming the problem of bacterial drug resistance.

Another objective of the present invention is to provide a bacteriostatic or bactericidal drug.

Another objective of the present invention is to provide a method of increasing sensitivity of bacteria to antibiotics.

Another objective of the present invention is to provide use of succinic acid in preparing a preparation or a medicine for clearance of biofilm bacteria.

In order to achieve the above-mentioned objectives, the present invention is achieved through the following solutions.

The present invention finds that the addition of succinic acid can increase sensitivity of clinical *Escherichia coli* to ampicillin, which has an antibiotic concentration gradient, succinic acid concentration gradient, and time effects.

The present invention finds that the addition of succinic acid can increase sensitivity of clinical *Escherichia coli* to other antibiotics (such as ampicillin, amoxicillin, penicillin G, gentamicin, ciprofloxacin, tetracycline, erythromycin, clindamycin, rifampin and etc.).

The above results show that the objective of treating drug-resistant bacteria can be achieved by combining antibiotics with succinic acid to increase the sensitivity of bacteria to the antibiotics.

The present invention finds that after adding succinic acid, ampicillin's bactericidal effect on other bacteria or drug-resistant bacteria (such as *Escherichia coli*, *Vibrio alginolyticus*, *Vibrio parahaemolyticus*, *Edwardsiella tarda*, *Pseudomonas aeruginosa*, and *Beta streptococcus*) is significantly improved, and the results show that succinic acid can increase the sensitivity of other bacteria or drug-resistant bacteria to ampicillin.

The present invention finds that succinic acid increases the content of antibiotics entering into the bacteria by increasing proton motive force of the bacteria, and eventually kills the bacteria.

The present invention prepares an in vitro clinical *Escherichia coli* biofilm, and proves that the method of combining succinic acid and ampicillin can effectively clear biofilm bacteria. A mouse chronic urinary tract infection model is further used, and clinical *Escherichia coli* biofilm is implanted in the urethra, followed by injection of succinic acid and ampicillin. It is found that an experimental group added with succinic acid and ampicillin has a significant bactericidal effect, which can significantly reduce drug-resistant bacteria on the biofilm, indicating that succinic acid can increase the sensitivity of clinical *Escherichia coli* biofilm to ampicillin. The above results show that combining succinic acid with antibiotics can clear drug-resistant bacteria in animal hosts.

In summary, the synergistic use of succinic acid and antibiotics can significantly increase the sensitivity of bacteria or drug-resistant bacteria to the antibiotics, thereby achieving the objective of highly effective bacteriostasis or bactericidal. Therefore, the present invention seeks for protection of use of succinic acid in increasing sensitivity of bacteria to an antibiotic.

Preferably, the bacteria are at least one of *Escherichia coli*, *Vibrio alginolyticus*, *Vibrio parahaemolyticus*, *Edwardsiella tarda*, *Pseudomonas aeruginosa*, and *Beta streptococcus*.

Preferably, the antibiotic is selected from at least one of ampicillin, amoxicillin, penicillin G, gentamicin, ciprofloxacin, tetracycline, erythromycin, clindamycin, and rifampin.

Preferably, it is use of succinic acid in increasing sensitivity of *Escherichia coli* to ampicillin.

Preferably, it is use of succinic acid in increasing sensitivity of *Escherichia coli* to amoxicillin, penicillin G, gentamicin, ciprofloxacin, tetracycline, erythromycin, clindamycin, or rifampin.

Preferably, it is use of succinic acid in increasing sensitivity of *Vibrio alginolyticus*, *Vibrio parahaemolyticus*, *Edwardsiella tarda*, *Pseudomonas aeruginosa*, or *Beta streptococcus* to ampicillin.

The present invention further seeks for protection of a bacteriostatic or bactericidal drug containing an antibiotic and succinic acid.

The present invention further seeks for protection of a method of increasing sensitivity of bacteria to an antibiotic which combining succinic acid with an antibiotic.

In the above-mentioned method, the bacteria are sensitive to bacteria or drug-resistant bacteria.

Preferably, the bacteria include but are not limited to *Escherichia coli*, *Vibrio alginolyticus*, *Vibrio parahaemolyticus*, *Edwardsiella tarda*, *Pseudomonas aeruginosa*, and *Beta streptococcus*. Since these bacteria are common human and farmed animal pathogenic bacteria, for example, *Escherichia coli*, *Vibrio alginolyticus*, *Vibrio parahaemolyticus*, *Edwardsiella tarda*, and *Pseudomonas aeruginosa* are Gram-negative bacteria, *Beta streptococcus* is Gram-positive bacteria. These bacteria can be drug-resistant bacteria or sensitive bacteria.

Preferably, the antibiotic is selected from but not limited to ampicillin, amoxicillin, penicillin G, gentamicin, ciprofloxacin, tetracycline, erythromycin, clindamycin, and rifampin. Ampicillin, amoxicillin, penicillin G are β-lactam antibiotics, gentamicin is an aminoglycoside antibiotic, ciprofloxacin is a quinolone antibiotic, tetracycline is a tetracycline antibiotic, erythromycin is a macrolide antibiotic, clindamycin is a lincosamide antibiotic, and rifampin is an anti-tuberculosis drug. These include main types of antibiotics currently in clinical use.

Preferably, a dose ratio of the succinic acid to the antibiotic is 1:0.0015 to 1:300 by weight.

Preferably, when the above-mentioned method is used to increase the sensitivity of bacteria to antibiotics, the usage amount of succinic acid is 3 mg to 30 g per administration.

The present invention further seeks for protection of use of succinic acid in preparing a preparation or a medicine for clearance of biofilm bacteria.

Preferably, the bacteria are clinical *Escherichia coli*.

Compared with the prior art, the present invention has the following beneficial effects.

The present invention finds firstly that succinic acid can increase the sensitivity of bacteria to antibiotics, thereby overcoming the problem of bacterial resistance. Further research finds that succinic acid can increase the content of antibiotics entering into the bacteria by increasing proton motive force of the bacteria. Combining succinic acid with antibiotics can significantly improve the bactericidal effect of the antibiotics, which has better effects and higher safety and operability compared with only using antibiotics as antibacterial drugs at present.

DESCRIPTION OF THE EMBODIMENTS

Figure 1:
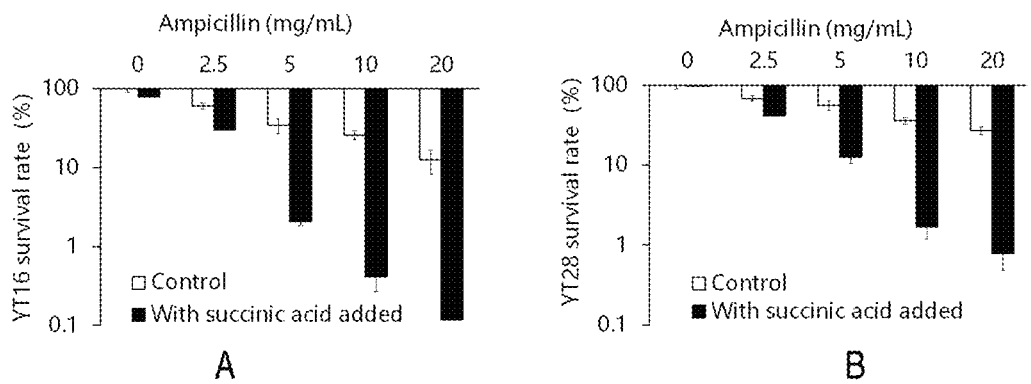
FIG. 1 illustrates the survival rate of clinical *Escherichia coli* after adding 20 mM succinic acid to ampicillin at different concentrations according to Embodiment 1, wherein A is for clinical *Escherichia coli* YT16, and B is for clinical *Escherichia coli* YT28.

The present invention is further described in detail below in combination with the accompanying drawings and specific embodiments, the embodiments are only used to explain the present invention, but not to limit the scope of the present invention. Unless otherwise specified, the test methods used in the following embodiments are conventional methods, and the materials and reagents used are reagents and materials available from commercial sources unless otherwise specified.

Embodiment 1 Succinic Acid Increases the Sensitivity of Clinical *Escherichia coli* to Ampicillin 1. Drug Resistance Analysis of Clinical *Escherichia coli*

*Escherichia coli* (*E. coli*) are one of the most common bacteria in the clinic. 30 strains of *E. coli* obtained from the clinic were named YT1-30. The minimum inhibitory concentrations (MIC) of 8 antibiotics against these 30 clinically obtained *E. coli* was detected according to the NCCLS method, and *E. coli* K12 was used as a control. The measurement results are shown in Table 1. It can be seen from these results that the MIC of these 30 strains are more than 4 times higher than the control *E. coli* K12 (except that the MIC of ceftazidime against YT1 is the same as the control), that is, the 30 clinical *E. coli* are all multiple drug-resistant bacteria, especially the MIC of ampicillin is 64 to 4000 times that of the control.

Table 1 Minimum inhibitory concentration (MIC) of 8 antibiotics against 30 clinical *Escherichia coli*

TABLE 1

Minimum inhibitory concentration (MIC) of 8 antibiotics against 30 clinical *Escherichia coli*

| | Amikacin | Ampicillin | Balofloxacin | Ceftazidime | Clindamycin hydrochloride | Gentamicin | Tetracycline | Roxithromycin |
|---|---|---|---|---|---|---|---|---|
| Control | 0.61 | 6.1 | 0.015 | 0.122 | 24.414 | 0.61 | 1.526 | 9.765 |
| YT1 | 9.765 | 25000 | 0.244 | 0.122 | 390.625 | 2.441 | 6.1 | 39.0625 |
| YT2 | 9.765 | 6250 | 3.906 | 0.488 | 390.625 | 156.25 | 24.414 | 625 |
| YT3 | 9.765 | 390.625 | 15.625 | 0.488 | 390.625 | 156.25 | 97.656 | 625 |
| YT4 | 9.765 | 6250 | 250 | 0.488 | 1562.5 | 9.765 | 390.625 | 156.25 |
| YT5 | 9.765 | 25000 | 250 | 7.81 | 6250 | 625 | 390.625 | 625 |
| YT6 | 9.765 | 1562.5 | 62.5 | 1.953 | 1562.5 | 156.25 | 97.656 | 625 |
| YT7 | 9.765 | 1562.5 | 15.625 | 0.488 | 6250 | 625 | 97.656 | 625 |
| YT8 | 9.765 | 1562.5 | 250 | 0.488 | 6250 | 625 | 97.656 | 625 |
| YT9 | 2.441 | 1562.5 | 250 | 0.488 | 1562.5 | 156.25 | 97.656 | 625 |
| YT10 | 39.0625 | 6250 | 15.625 | 7.812 | 6250 | 625 | 97.656 | 625 |
| YT11 | 2500 | 1562.5 | 3.906 | 7.812 | 25000 | 2500 | 97.656 | 625 |
| YT12 | 2500 | 6250 | 62.5 | 0.488 | 25000 | 2500 | 6250 | 625 |
| YT13 | 2500 | 6250 | 62.5 | 0.488 | 25000 | 2500 | 6250 | 625 |
| YT14 | 2500 | 6250 | 15.625 | 0.488 | 25000 | 2500 | 6250 | 2500 |
| YT15 | 2500 | 6250 | 15.625 | 0.488 | 25000 | 2500 | 6250 | 2500 |
| YT16 | 2500 | 6250 | 250 | 0.488 | 25000 | 2500 | 6250 | 625 |
| YT17 | 2500 | 6250 | 250 | 0.488 | 25000 | 2500 | 6250 | 625 |
| YT18 | 2.441 | 6250 | 62.5 | 0.488 | 390.625 | 2.441 | 1562.5 | 625 |
| YT19 | 9.76 | 1562.5 | 62.5 | 0.488 | 390.625 | 625 | 1562.5 | 625 |
| YT20 | 2.441 | 1562.5 | 62.5 | 0.122 | 390.625 | 156.25 | 1562.5 | 625 |
| YT21 | 2500 | 1562.5 | 15.625 | 0.488 | 390.625 | 2500 | 1562.5 | 625 |
| YT22 | 625 | 6250 | 62.5 | 0.488 | 390.625 | 2500 | 1562.5 | 625 |
| YT23 | 9.765 | 1562.5 | 15.625 | 0.488 | 390.625 | 156.25 | 1562.5 | 625 |
| YT24 | 9.765 | 6250 | 15.625 | 7.812 | 390.625 | 625 | 1562.5 | 625 |
| YT25 | 2500 | 6250 | 0.244 | 31.25 | 390.625 | 2500 | 6.103 | 625 |
| YT26 | 2500 | 6250 | 15.625 | 31.25 | 390.625 | 2500 | 97.656 | 625 |
| YT27 | 9.765 | 6250 | 15.625 | 0.488 | 390.625 | 625 | 97.656 | 625 |
| YT28 | 2500 | 1562.5 | 15.625 | 31.25 | 1562.5 | 2500 | 390.625 | 2500 |
| YT29 | 9.765 | 6250 | 15.625 | 7.812 | 390.625 | 625 | 390.625 | 625 |
| YT30 | 2.441 | 25000 | 15.625 | 7.812 | 390.625 | 39.0625 | 390.625 | 156.25 |

2. Preparation of Test Samples

In order to study whether succinic acid can increase the sensitivity of clinical *Escherichia coli* to ampicillin, two (YT16 and YT28) out of 30 clinical strains were selected to further study the effects of clinical bacteria on increasing of the sensitivity to ampicillin at different concentrations of succinic acid, different concentrations of antibiotics, and different action times.

A single colony of clinical bacteria was picked from a solid LB plate and was inoculated in 5 mL LB liquid medium for culture at 37° C. and 200 rpm for 16 hours, and then was inoculated in 100 mL LB liquid medium at a ratio of 1:100 (v/v) and was cultured at 37° C. until $OD_{600}$ value was 1.0. 20 mL of bacterial solution was collected and centrifuged at 8000 rpm for 5 minutes, the supernatant was cleared and bacterial cells were washed with an equal volume of 0.85% normal saline, and finally the bacterial cells were suspended with 1×M9 basic medium (containing 10 mM acetate), the OD value of the bacterial solution was adjusted to 0.5, and then 5 mL of the bacterial solution was aliquoted in a test tube for the following experimental studies.

3. Succinic Acid Increasing the Sensitivity of Clinical Bacteria to Antibiotics has an Antibiotic Concentration Gradient Effect In order to understand the effect of succinic acid on increasing the sensitivity of clinical bacteria to antibiotics at different antibiotic concentrations, 20 mM succinic acid and four concentrations of ampicillin (2.5, 5, 10, and 20 mg/mL) were set to treat the bacteria for 4 hours, followed by counting viable bacteria. The survival rates of the clinical bacteria in medium with adding succinic acid and without adding succinic acid at the same antibiotic concentration were compared.

The results show that after adding succinic acid, as the concentration of ampicillin increases, the bactericidal efficiency of clinical bacteria increases more significantly. Details are as follows.

For the clinical strain YT16 (as shown in A of FIG. 1), after adding 20 mM succinic acid, when the ampicillin concentration was 2.5 mg/mL, the bactericidal efficiency increased by more than 2 times (the survival rate decreased from 61.04% without adding succinic acid to 30.06% after adding succinic acid; when the ampicillin concentration was 5 mg/mL, the bactericidal efficiency of clinical bacteria increased to 16.75 times (the survival rate decreased from 34.53% without adding succinic acid to 2.06% after adding succinic acid); when the ampicillin concentration was 10 mg/mL, the bactericidal efficiency of clinical bacteria increased by 62.25 times (the survival rate decreased from 25.99% without adding succinic acid to 0.41% after adding succinic acid); and when the ampicillin concentration was 20 mg/mL, the bactericidal efficiency of clinical bacteria increased by 105.96 times (the survival rate decreased from 12.47% without adding succinic acid to 0.12% after adding succinic acid).

For the clinical strain YT28 (as shown in B of FIG. 1), after adding 20 mM succinic acid, when the ampicillin concentration was 2.5 mg/mL, the bactericidal efficiency increased by more than 1.65 times (the survival rate decreased from 68.38% without adding succinic acid to 41.62% after adding succinic acid); when the ampicillin concentration was 5 mg/mL, the bactericidal efficiency of clinical bacteria increased to 4.42 times (the survival rate decreased from 56.25% without adding succinic acid to 12.71% after adding succinic acid); when the ampicillin concentration was 10 mg/mL, the bactericidal efficiency of clinical bacteria increased by 21.06 times (the survival rate decreased from 35.87% without adding succinic acid to 1.7% after adding succinic acid); and when the ampicillin concentration was 20 mg/mL, the bactericidal efficiency of clinical bacteria increased by 34.48 times (the survival rate decreased from 27.09% without adding succinic acid to 0.79% after adding succinic acid).

4. Succinic Acid Increasing the Sensitivity of Clinical Bacteria to Antibiotics has a Time Effect In order to further understand whether the effect of succinic acid on increasing the sensitivity of clinical bacteria to antibiotics has a time effect, when 20 mM succinic acid and 10 mg/mL ampicillin were added, viable bacteria were counted within 1 to 7 hours, and the relationship between bactericidal efficiency and time was observed.

Figure 2:
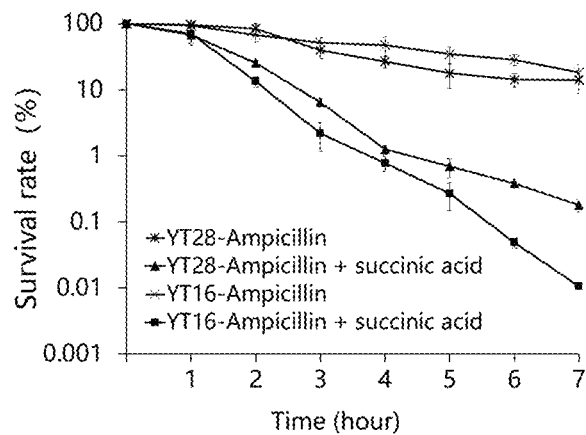
FIG. 2 illustrates the survival rate of clinical *Escherichia coli* YT16 and YT28 at different times after adding 20 mM succinic acid to 10 mg/mL ampicillin according to Embodiment 1.

The results are shown in FIG. 2. After adding succinic acid to the clinical bacteria based on the addition of ampicillin, the number of viable bacteria decreased significantly with time.

For YT16, the bactericidal efficiency is only 1.33 time at 1 hour (the survival rate decreased from 93.89% with only ampicillin added to 71.54% after adding ampicillin and succinic acid), the bactericidal efficiency reached 60.66 times at 4 hour (the survival rate decreased from 47.34% to 0.78%), and the bactericidal efficiency reached 1744.19 times at 7 hours (the survival rate decreased from 18.45% to 0.01%).

For YT28, the bactericidal efficiency is only 1.44 time at 1 hour (the survival rate decreased from 96.79% to 66.81%), the bactericidal efficiency reached 21.45 times at 4 hours (the survival rate decreased from 26.79% to 1.25%), and the bactericidal efficiency reached 78.34 times at 7 hours (the survival rate decreased from 14.18% to 0.18%).

5. Succinic Acid Increasing the Sensitivity of Clinical Bacteria to Antibiotics has Concentration Dependence In order to understand whether there is a gradient effect between succinic acid concentration and bactericidal efficiency and its optimal bactericidal concentration, based on the addition of 10 mg/mL ampicillin, different concentrations (1.25 mM to 20 mM) of succinic acid were added for action for 4 hours, and then the viable bacteria were counted, and the survival rate was calculated. The formula is the number of viable bacteria when different concentrations of succinic acid were added/the number of viable bacteria without adding succinic acid×100%.

Figure 3:
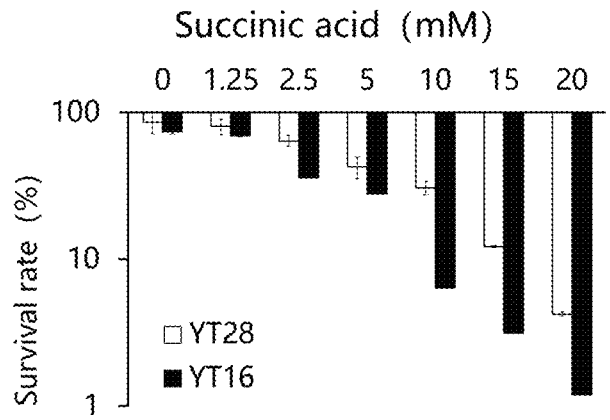
FIG. 3 illustrates the survival rate of clinical *Escherichia coli* YT16 and YT28 after adding different concentrations of succinic acid to 10 mg/mL ampicillin according to Embodiment 1.

The results are shown in FIG. 3. The survival rate of YT16 without adding succinic acid was 73.8%, and with the increase of succinic acid concentration from 1.25-20 mM, the bacterial survival rate decreased from 69.23% to 1.19%, and the bactericidal efficiency increased from 1.07 times to 61 times. The survival rate of YT28 without adding succinic acid was 86.21%, and with the increase of succinic acid concentration from 1.25-20 mM, the bacterial survival rate decreased from 80.31% to 4.24%, and the bactericidal efficiency increased from 1.07 times to 20 times.

6. Succinic Acid Increasing the Sensitivity of Clinical *Escherichia coli* to Ampicillin is Ubiquitous In order to study whether the sensitivity of clinical *Escherichia coli* with different drug-resistance to ampicillin was increased after adding succinic acid, samples of the remaining 28 strains of clinical bacteria were prepared according to step 2 of the present embodiment, 20 mM succinic acid and 10 mg/mL ampicillin were added respectively, after action for 4 hours, the number of viable bacteria was counted, and the survival rate was calculated.

Figure 4:
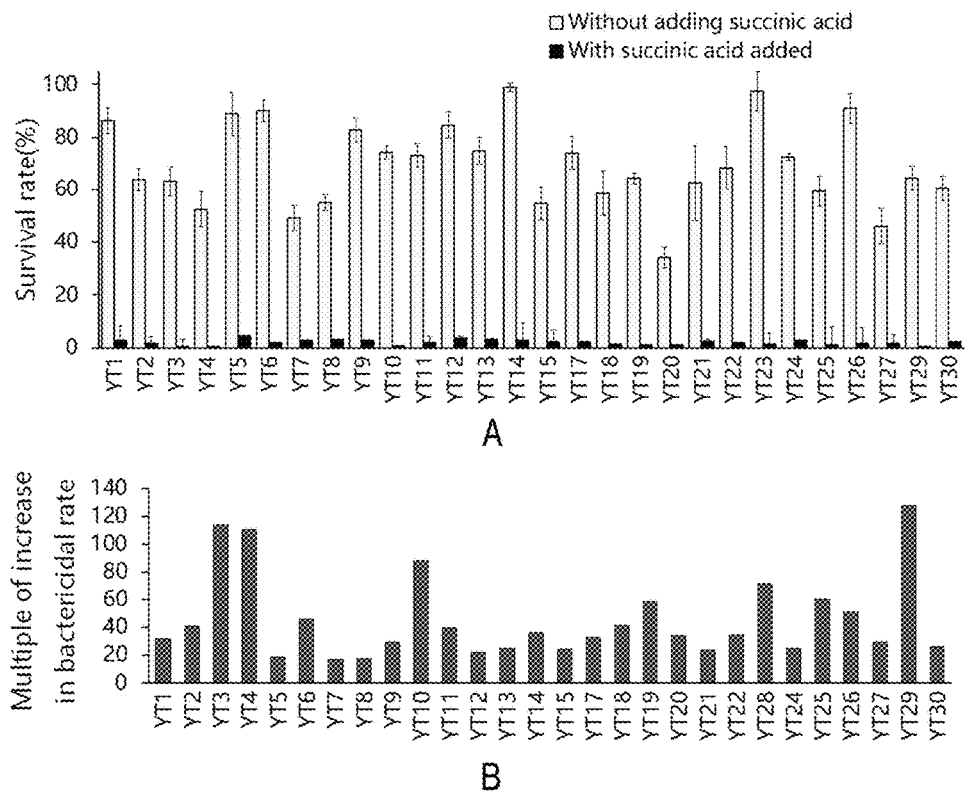
FIG. 4 illustrates the multiple of increase in the survival rate and bactericidal rate of 28 strains of clinical *Escherichia coli* after adding 20 mM succinic acid to 10 mg/mL ampicillin according to Embodiment 1, wherein A is for the multiple of increase in the survival rate, and B is the multiple of increase in the bactericidal rate.

The results are shown in FIG. 4. Succinic acid can increase the sensitivity of all clinical bacteria to ampicillin (as shown in A of FIG. 4), the degree that succinic acid increases the sensitivity is different, and the sensitivity increased between 17 times and 127 times (as shown in B of FIG. 4).

Embodiment 2 Succinic Acid Increases the Sensitivity of Clinical Drug-Resistant Bacteria *Escherichia coli* to Other Antibiotics 1. Increasing the Sensitivity to Penicillin Antibiotics In order to study whether clinical *Escherichia coli* has effect on penicillin antibiotics after adding succinic acid, two clinical *Escherichia coli* samples of YT16 and YT28 were prepared according to step 2 in Embodiment 1, 20 mM succinic acid and 3 kinds of penicillin were added respectively, after action for 4 hours, the number of viable bacteria was counted, and the survival rate was calculated.

The results show that succinic acid can increase the sensitivity of clinical *Escherichia coli* YT16 and YT28 to these three antibiotics. Details are as follows.

Figure 5:
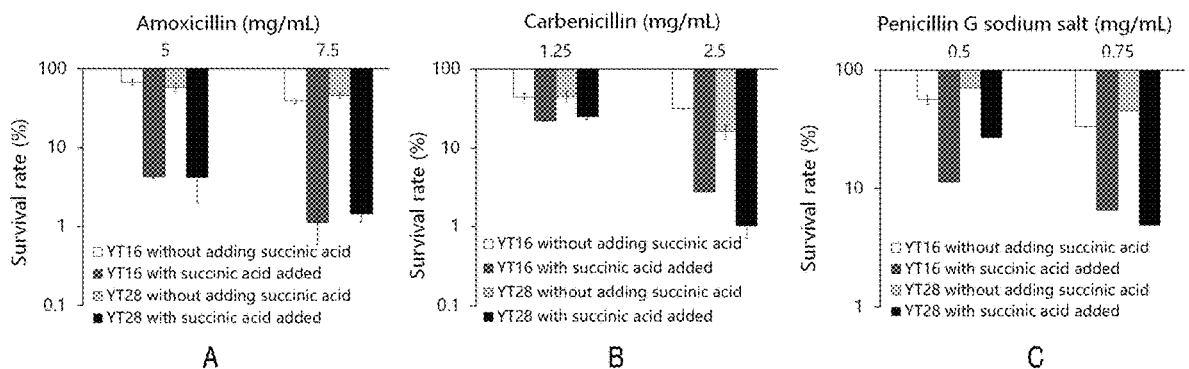
FIG. 5 illustrates the survival rate of clinical *Escherichia coli* YT16 and YT28 after adding 20 mM succinic acid to different penicillin antibiotics according to Embodiment 2, wherein A is for amoxicillin, B is for carbenicillin, and C is for penicillin G sodium salt.

For amoxicillin, after adding 20 mM succinic acid, adding 5 mg/mL amoxicillin can increase the sensitivity of YT16 and YT28 by 15.86 and 13.94 times, respectively; and adding 7.5 mg/mL amoxicillin can increase the sensitivity of YT16 and YT28 by 3.37 and 31.85 times, respectively (as shown in A of FIG. 5).

For carbenicillin, after adding 20 mM succinic acid, adding 1.25 mg/mL carbenicillin can increase the sensitivity of YT16 and YT28 by 1.99 and 1.8 times, respectively; and adding 2.5 mg/mL carbenicillin can increase the sensitivity of YT16 and YT28 by 11.65 and 15.85 times, respectively (as shown in B of FIG. 5).

For penicillin G sodium salt, after adding 20 mM succinic acid, adding 0.5 mg/mL penicillin G sodium salt can increase the sensitivity of YT16 and YT28 by 4.96 and 2.66 times, respectively; and adding 0.75 mg/mL penicillin G sodium salt can increase the sensitivity of YT16 and YT28 by 5.13 and 9.34 times, respectively (as shown in C of FIG. 5).

2. Increasing the Sensitivity to Other Antibiotics

In order to study whether clinical *Escherichia coli* is effective against antibiotics other than penicillin antibiotics after adding succinic acid, YT16 sample was prepared according to step 2 in Embodiment 1, 20 mM succinic acid and several kinds of antibiotics (gentamicin, ciprofloxacin, tetracycline, erythromycin, clindamycin, and rifampin) were added respectively, after action for 4 hours, the number of viable bacteria was counted, and the survival rate was calculated.

Figure 6:
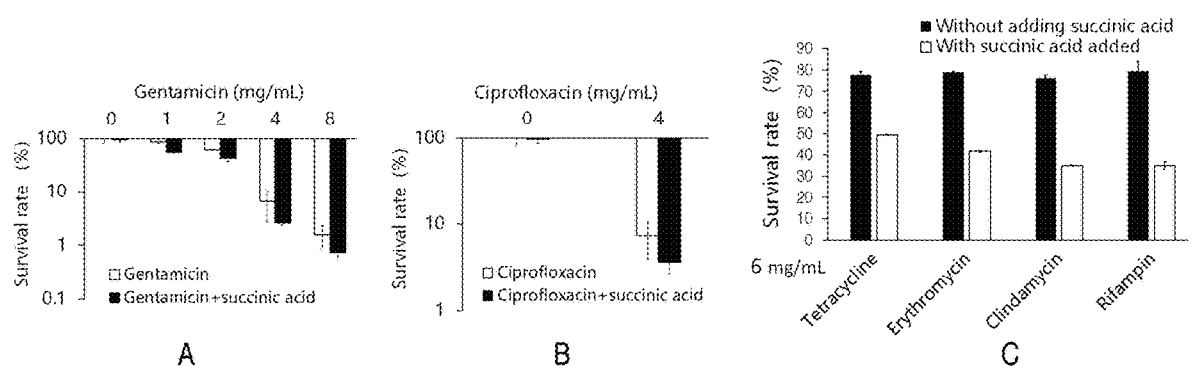
FIG. 6 illustrates the survival rate of clinical *Escherichia coli* YT16 after adding 20 mM succinic acid to different antibiotics according to Embodiment 2, wherein A is for gentamicin, B is for ciprofloxacin, and C is for tetracycline, erythromycin, clindamycin, and rifampin.

The results are shown in FIG. 6. Succinic acid can enhance the sensitivity of YT16 to these different kinds of antibiotics by about 2 times.

Embodiment 3 Succinic Acid Increases the Sensitivity of Many Bacteria to Ampicillin Several kinds of bacteria, such as *Escherichia coli, Vibrio alginolyticus, Vibrio parahaemolyticus, Edwardsiella tarda, Pseudomonas aeruginosa, Beta streptococcus*, were picked, monocloned into 100 mL LB liquid medium, and cultured at 37° C. or 30° C. and 200 rpm for 16 hours to reach saturation condition. 20 mL of bacterial solution of each bacteria was collected respectively and centrifuged at 8000 rpm for 5 minutes, the supernatant was cleared and bacterial cells were washed with an equal volume of 0.85% normal saline, and finally the bacterial cells were suspended with 1×M9 basic medium (containing 10 mM acetate), the OD value of the bacterial solution was adjusted to 0.5, and then 5 mL of the bacterial solution was aliquoted in a test tube for future use.

The prepared bacterial solution mentioned above was divided into 2 groups according to the type of bacteria: the control group (only added ampicillin) and the experimental group (added ampicillin and succinic acid). 20 mM succinic acid and ampicillin at 2 times the minimum inhibitory concentration of the respective bacteria were added, after 4 hours of incubation at 37° C. and 200 rpm in a shaker, 100 μL of the bacterial solution was taken to count viable bacteria and calculate its survival rate.

Figure 7:
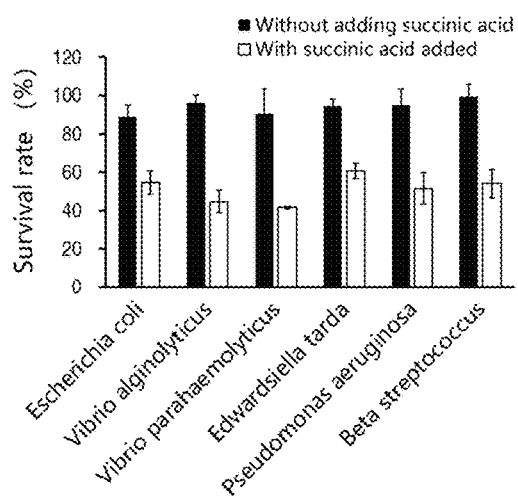
FIG. 7 illustrates the survival rate of different bacteria after adding 20 mM succinic acid to ampicillin according to Embodiment 3.

The results are shown in FIG. 7. After adding succinic acid, the sensitivity of these bacteria to ampicillin generally increased by 1.5 to 2.2 times.

In summary, the addition of succinic acid can not only increase the sensitivity of clinical *Escherichia coli* to ampicillin, but also have similar effects on the other three penicillin antibiotics, and can also increase the sensitivity of clinical *Escherichia coli* to other antibiotics. Succinic acid can also increase the sensitivity of several kinds of bacteria to ampicillin. The above results show that the to the sensitivity of bacteria to antibiotics can be increased by the method of combining antibiotics with succinic acid to achieve the objective of treating bacteria (including clinical *Escherichia coli* drug-resistant bacteria).

Embodiment 4 Succinic Acid May Improve Clearance Efficiency of Clinical *Escherichia coli* Biofilms 1. Preparation of Clinical *Escherichia coli* Biofilms 9 strains of clinical *Escherichia coli* (YT3, YT11, YT12, YT16, YT17, YT21, YT22, YT23, YT28, YT33) were picked, monocloned into LB medium, and cultured overnight, then were transferred into 2 mL fresh LB medium at 1:200, and added with a 6 mm PE-50 biological catheter that was sterilized by UV, and cultured in a 37° C. incubator for culture for 24 hours. The bacterial solution was replaced with 1 mL of LB medium daily, and the catheter was continuously cultured for 3 days. The prepared biofilm was washed 5 times with 1 mL of sterile normal saline, and then placed in a 1.5 mL EP tube.

2. In Vitro Bactericidal Assay of Biofilm

The assay was divided into 4 groups: normal saline control group, succinic acid group, ampicillin group, ampicillin+succinic acid group, and the catheters were treated in a shaker at 37° C. and 200 rpm. A dosage of succinic acid was 580 mg/kg, and a dosage of ampicillin was 2000 mg/kg for YT16, and 500 mg/kg for YT28. After 6 hours, ultrasonic cleaning was conducted for 15 minutes, the biofilm on the catheter was eluted and thoroughly mixed, and after gradient dilution, spot plate counting was performed. The formula for calculating the bacterial survival rate is: number of viable bacteria in each group/number of viable bacteria in the control group×100%.

Figure 8:
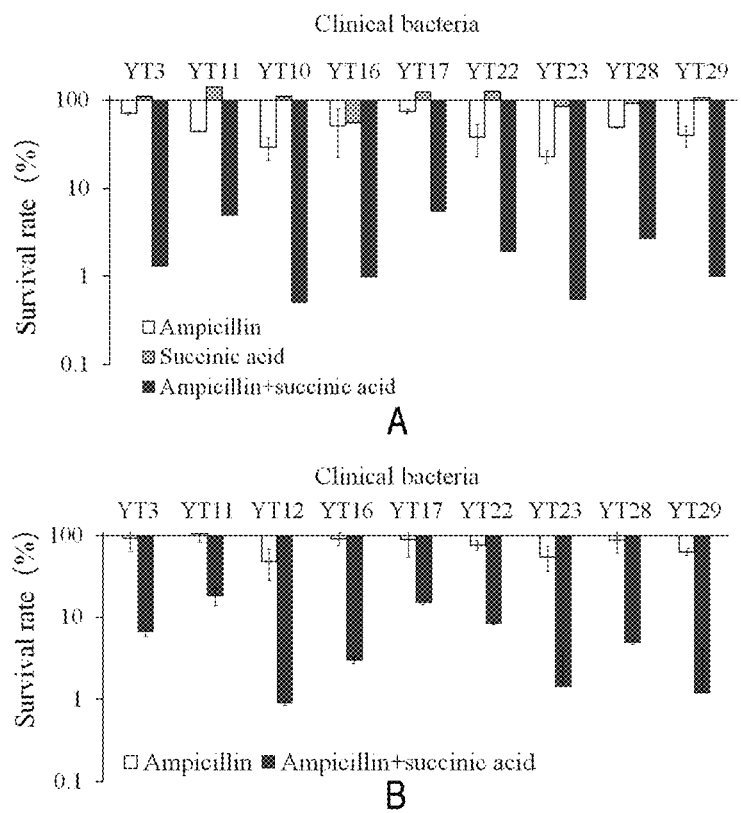
FIG. 8 illustrates the therapeutic effect of combining succinic acid with ampicillin on clinical *Escherichia coli* according to Embodiment 4, wherein A is for the result of in vitro bactericidal assay of clinical *Escherichia coli* biofilm, and B is for the clearance effect of drug-resistant bacteria in urethra and kidneys of mice.

The bacterial survival rate on the biofilms of the three experimental groups is shown in A of FIG. 8, and it can be seen the results that: (1) using succinic acid or ampicillin alone cannot clear clinical *Escherichia coli* on the biofilms; and (2) only when succinic acid and ampicillin are used in combination, the clinical *Escherichia coli* can be cleared with an obvious clearance efficiency which can be increased by 9 to 106 times.

3. Succinic Acid May Improve In Vivo Clearance Effect of Ampicillin on Drug-Resistant Bacteria Further, mice were used as test animals, and the prepared clinical *Escherichia coli* biofilm was implanted into the mouse urethra to construct a mouse chronic urinary tract infection model for conducting an in vivo clinical *Escherichia coli* clearance test was performed: a 6-mm PE-50 biological catheter of a clinical *Escherichia coli* biofilm formed by culture for 3 days was implanted into the urethra of a 5-week-old Kunming female mouse (about 20 g). After 48 hours, mice were divided into 2 groups of 5 mice each, which were the ampicillin group and the ampicillin+succinic acid group. Mice were injected intraperitoneally with 590 mg/kg succinic acid and an appropriate amount of ampicillin antibiotic (injected with 2000 mg/kg for the bacteria that MIC=6250 μg/mL, injected with 500 mg/kg for the bacteria that MIC=1560 μg/mL) twice a day for 3 consecutive days. 24 hours after the last injection, the catheter tube was taken into normal saline to suspend the biofilm bacteria in the ultrasound, and gradient dilution and plate counting were performed to calculate the bacterial survival rate on the catheter biofilm. The calculation formula is the number of viable bacteria in the injection substance group/number of viable bacteria in the control group×100%.

As shown in B of FIG. 8, the results show that the addition of antibiotics while adding succinic acid can significantly reduce the drug-resistant bacteria on the biofilm, and the bactericidal efficiency of the 9 strains increased by 14, 5, 53, 30, 5, 9, 38, 17, and 53 times, respectively. Combined with the above biofilm test results, it is illustrated that succinic acid can increase the sensitivity of clinical *Escherichia coli* biofilms to ampicillin.

Embodiment 5 Succinic Acid Increases the Content of Ampicillin in Clinical *Escherichia coli*

Bacterial death is related to the amount of antibiotics entering into the bacteria. Bacterial drug-resistance is due to the concentration of antibiotics entering into the bacteria is lower than the concentration that caused them to die. In order to study the mechanism by which succinic acid increases the sensitivity of clinical *Escherichia coli* to antibiotics, and to verify whether it works by increasing the amount of antibiotics entering into the bacteria, bacterial samples were prepared according to the method of step 2 of Embodiment 1, and the experiment was divided into 2 groups: 1 control group (only adding ampicillin) and 1 experimental group (adding ampicillin and succinic acid), for incubation at 37° C. and 200 rpm in a shaker for 6 hours. The cultured bacteria were washed and resuspended in normal saline, $OD_{600}$ value was adjusted to 1.0, and 1 mL of bacterial cells were taken for ultrasonication, and after centrifugation, the supernatant was taken to determine the antibiotic content. The ampicillin ELISA rapid diagnostic kit (purchased from Shenzhen Lvshiyuan Biotechnology Co., Ltd., with a detection range of 2 to 1000 g/mL) was used for detection and the specific steps are as follows: 50 μL of sample (or standard) and 50 μL of antibody were added into a 96-well plate, mixed gently, and incubated at 25° C. for 30 minutes, and the plate was washed 4 to 5 times; 100 μL of enzyme standard was added, mixed gently, and incubated away from light at 25° C. for 30 minutes, and the plate was washed 4 to 5 times; 50 μL of substrates A and B was added respectively, mixed gently, and incubated away from light at 25° C. for 15 minutes; and finally, a stop solution was added to stop the reaction, and an enzyme-labeled instrument was set to measure the absorbance of the reaction product at 450 nm. A standard curve was drawn, with the percent absorbance of the standard as an ordinate and semi-log of the concentration of the ampicillin standard (ng/mL) as the abscissa. AMP actual concentration=sample detection concentration xdilution multiple.

Figure 9:
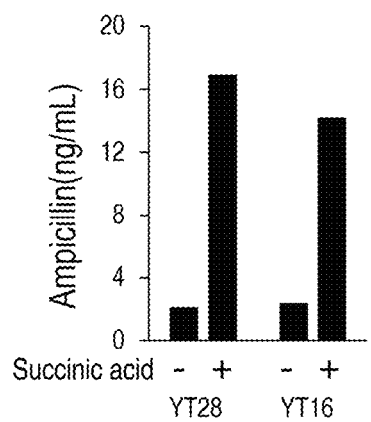
FIG. 9 illustrates the change of content of ampicillin in bacteria after adding succinic acid to ampicillin according to Embodiment 5.

The results are shown in FIG. 9. The number of antibiotics in the bacteria in the experimental group with ampicillin and succinic acid increased by 5.97 times for YT16 and by 7.99 times for YT28 compared with the control group with only ampicillin. The results show that succinic acid does increase the number of antibiotics entering into the bacteria.

Embodiment 6 Succinic Acid Increases Proton Motive Force of Clinical *Escherichia coli*

According to Embodiment 5, after adding succinic acid, the number of antibiotics entering into clinical *Escherichia coli* has increased significantly, but the specific mechanism of action is still unclear. In order to study the mechanism of action of succinic acid to promote the entry of antibiotics into the bacteria, the experiment (the preparation of experimental samples was performed according to the method of step 2 of Embodiment 1) was divided into 2 groups: 1 control group (without adding ampicillin and succinic acid) and 1 experimental group (with succinic acid added), for incubation at 37° C. and 200 rpm in a shaker for 6 hours. A concentration of the treated bacteria was adjusted to 106 CFU/mL, 1 mL of the treated bacteria was taken and transferred into a 1.5 mL EP tube, 10 μL of 3 mM DiOC2 (3,3'-diethyloxa-carbocyanine iodide) was added, and oscillation and incubation were performed for 30 minutes after mixing sufficiently. The bacteria were transferred to a flow cytometry analysis tube before use on the machine, a FACSCalibur flow cytometer (Becton Dickinson, San Jose, Calif., USA) was used for detection, and parameter settings were performed according to the instrument operating procedures. The dye DiOC2 (3) has a green fluorescence excitation wavelength of 488 nm, an emission wavelength of 530 nm, a red fluorescence excitation wavelength of 488 nm, and an emission wavelength of 610 nm. The ratio of the red light intensity to the green light intensity indicates the intensity of the membrane potential, and calculation formula of the proton motive force (PMF) value is LOG ($10^{3/2}$*Y mean/X mean). Y mean and X mean represent red light intensity and green light intensity, respectively. Determination was performed according the instructions of the BacLight bacterial membrane potential kit (Invitrogen) kit.

Figure 10:
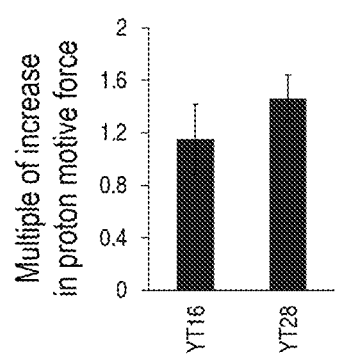
FIG. 10 illustrates the change of bacterial proton motive force after adding succinic acid according to Embodiment 6.

The results are shown in FIG. 10, and it was found that the proton motive force of the bacteria increased 1.2 times (YT16) and 1.45 times (YT28) after adding succinic acid. This result indicates that the addition of succinic acid can cause an increase in the proton motive force of the bacteria, thereby increasing the content of antibiotics entering into the bacteria and eventually causing the bacteria to die.

Finally, it's worth noting that the above embodiments are only used to explain the technical solution of the present invention, and not to limit the scope of protection of the present invention. It is possible for those of ordinary skill in the art to make other changes or variation in different forms based on the above description and ideas, and it is not necessary or impossible to exhaust all implementations herein. Any modifications, equivalent replacements, and improvements made within the spirit and principles of the present invention should be included within the scope of protection of the claims of the present invention.

What is claimed is:

1. A method of increasing bactericidal effect of an antibiotic, comprising:
    administering a combination of succinic acid and the antibiotic to bacteria in M9 medium, wherein in the M9 medium the succinic acid increases sensitivity of the bacteria to the antibiotic and an amount of the antibiotic entering into the bacteria,
    wherein the antibiotic comprises ampicillin, penicillin, amoxicillin, carbenicillin, penicillin G sodium salt, gentamicin, ciprofloxacin, tetracycline, erythromycin, clindamycin and rifampin.

2. The method according to claim 1, wherein the bacteria are sensitive bacteria or drug-resistant bacteria.

3. The method according to claim 1, wherein the bacteria are at least one of *Escherichia coli, Vibrio alginolyticus, Vibrio parahaemolyticus, Edwardsiella tarda, Pseudomonas aeruginosa*, and *Beta streptococcus*.

4. The method according to claim 1, wherein the antibiotic is selected from at least one of ampicillin, amoxicillin, penicillin G, gentamicin, ciprofloxacin, tetracycline, erythromycin, clindamycin, and rifampin.

5. The method according to claim 1, wherein a dose ratio of the succinic acid to the antibiotic is 1:0.0015 to 1:300 by weight.

6. The method according to claim 1, wherein succinic acid is administered in an amount of from 3 mg to 3 g.

7. The method according to claim 2, wherein the bacteria are at least one of *Escherichia coli, Vibrio alginolyticus, Vibrio parahaemolyticus, Edwardsiella tarda, Pseudomonas aeruginosa*, and *Beta streptococcus*.

8. The method according to claim 2, wherein the antibiotic is selected from at least one of ampicillin, amoxicillin, penicillin G, gentamicin, ciprofloxacin, tetracycline, erythromycin, clindamycin, and rifampin.

* * * * *